United States Patent [19]

Hester

[11] Patent Number: 5,788,170
[45] Date of Patent: Aug. 4, 1998

[54] SATCHEL FOR REFEREE'S NEEDS AND ACCESSORIES

[76] Inventor: Beulah C. Hester, 314 Redwood Dr., Stanford, Ky. 40484

[21] Appl. No.: 503,365

[22] Filed: Jul. 17, 1995

[51] Int. Cl.$^6$ .................................................. A45F 3/00
[52] U.S. Cl. .................... 224/684; 224/674; 224/677; 224/681; 224/919
[58] Field of Search .................... 224/919, 932, 224/660, 674, 676, 680, 681, 682, 683, 684, 251, 600; 150/145, 147; D3/221, 226, 227

[56] References Cited

U.S. PATENT DOCUMENTS

| | | | |
|---|---|---|---|
| D. 255,509 | 6/1980 | Nathan et al. | D3/226 |
| D. 355,070 | 2/1995 | Thiesen | D3/225 |
| 367,996 | 8/1887 | Nathan | 224/684 |
| 1,432,032 | 10/1922 | Patzkowski | 224/600 |
| 2,568,382 | 6/1951 | Previdi | 224/684 |
| 2,682,981 | 7/1954 | Previdi | 224/684 |
| 2,983,412 | 5/1961 | Ferguson | 224/683 |
| 3,755,858 | 9/1973 | McPhaul | 224/932 |
| 4,693,402 | 9/1987 | Comeau | 224/919 |
| 4,796,790 | 1/1989 | Hamilton | 224/680 |
| 5,020,673 | 6/1991 | Adams | 150/145 |
| 5,244,136 | 9/1993 | Collaso | 224/676 |

*Primary Examiner*—Henry J. Recla
*Assistant Examiner*—Gregory M. Vidovich
*Attorney, Agent, or Firm*—M. Conrad Huffstutler

[57] ABSTRACT

Umpire's satchel with multiple fitted compartments for required equipment items, ID cards, first-aid supplies, hygiene items is disclosed. An external anchor for an absorbent wiper is provided. The satchel can be prepared in mirror-image models for right- or left-handed individuals. Optional features such as badge window and frontwall expansion pleat are also disclosed. Alternative custom configurations and embodiments with a removable panel of customized fitted compartments are indicated. Safety provisions for handling contaminated gameballs and HIV biohazards are disclosed.

10 Claims, 5 Drawing Sheets

SATCHEL FOR REFEREE'S NEEDS AND ACCESSORIES

BACKGROUND OF THE INVENTION

This invention relates particularly to a flexible, expandable satchel for use by male or female referees of games in which a ball is used. While on duty, such monitors or field judges are required to carry on their person at all times various small items of measuring equipment, one or more extra balls and any accessory items they may desire for their personal comfort and safety during the course of the game. In certain professional sports such as soccer or American baseball, spectators or participants may subject officials to various types of physical abuse which can lead to life-threatening injury. For these high-risk situations, the referee might need to carry not only items for individual hygiene but also first-aid supplies or a defense spray.

The main market for this invention is trained, league-certified umpires who serve commercial teams or non-professional athletes. Although men make up the majority of this group, the number of active women umpires is growing rapidly. It is no surprise, therefore, that previous "ball bags" worn by male officials tended to be small, simple "waterproof pouches" for carrying 1-3 extra balls, some of which might be soiled with mud or slime. Because the role of the field judge may require extended exposure to intense sun or rain and is often 100-200 meters out on the playing field, there is a need for an improved, fitted satchel which includes appropriate special-purpose compartments to hold standard items such as the photo-ID card for field security, which can be displayed at all times. In addition to personal-hygiene supplies such as hair comb, tissues, catamenial tampons, sunscreen and lip balm, modern referees need compartments designed to carry counters, brushes, writing pads, score sheets or even a handheld computer for immediate, easy one-hand access.

A special need that was first recognized about 1988 is the need of umpires to protect themselves against AIDS/HIV infections which can be transmitted by body fluids/discharges of the players carried upon the surface of the balls and other equipment used—and handled by the officials—during a game. This biohazard imposes the requirement for continuing use of protective gloves by the referee, special virucide surface treatments for every ball handled, and sealed, individual, disposable, impermeable bags to hold treated balls ready to be put back into play. It is conceivable that certain league rules may require that a quantity of virucide-pretreated balls be prepared and sealed into individual, tamper-evident bags prior to beginning of play. For the referee's safety, it would be desirable: (a) to handle in-play balls only with gloved hands and (b) to secure contaminated balls removed from play immediately in special closed decontamination containers.

For optimum ease of use, the satchel must have several special-purpose compartments placed, sized and oriented so that access to its contents, such as a strike counter, is fast and sure and the device is withdrawn ready for instant use already in the preferred hand of the user. Conversely, each compartment must contain a specific equipment item securely so that it is not lost or damaged due to running or other quick movements. Frequently, the official may also be required to carry a rule book and possibly statistical data for the field, teams and specific players. Finally, the physical appearance of the umpire satchel, especially color and decorations must conform to apparel codes imposed by the league or long traditions of the sport relative to umpire dress and modesty.

These specific, umpire satchel requirements are easily distinguished from the needs of a tennis player who must carry several new tennis balls for a typical service. In the case of a ball-holder worn by a lady tennis player, the only function is to hold 2 tennis balls and the main consideration is lightness, low bulk and comfort during rapid, forceful motions typical of competitive play. Waist-suspended ball holders which are heavy, sharp-cornered and bulky may hinder the player's responses or her degree of concentration. Occasionally, a typical holder will release a ball during active play which can cause a fall or delay the game. U.S. Pat. No. 3,865,290 is an example of a tennis-ball holder which attaches to the player's clothing by means of a keyhole and locking flange ring. The present umpire satchel serves a different set of needs and is therefore different in both size and design concepts.

Similarly, the design of an umpire's satchel is easily distinguished from the construction of a reinforced, equipment duffel bag such as used by a volunteer "Little-League" team manager to transport the balls, bats, gloves, masks, etc., to the playing field. Shoulder-strap carriers such as those disclosed in U.S. Pat. No. 4,793,532 are used to carry 1–10 bats, a like number of balls and other team-equipment items totaling about 25–50 Kg. The present umpire satchel serves a different set of needs and is therefore different in both size and design concepts.

SUMMARY OF THE INVENTION

The main object of this invention is a satchel with fitted compartments for carrying items of required equipment and other personal supplies to be used by a game referee or field judge. The compartments are fitted to each specific item of equipment and to the personal preferences of the user so that every equipment item is immediately available for instant use or display by either a right- or left-handed person.

Another object of this invention is to provide a set of compartments to contain specific personal hygiene supplies for easy, one-hand access.

A further object of this invention is to provide a set of compartments to contain specific first-aid and personal defense supplies also immediately available by one-hand access.

An additional object of this invention is to provide a set of fitted compartments for an umpire satchel wherein each compartment is adapted for independent size and shape adjustments.

A further additional object of this invention is to provide a set of fitted compartments removably attached to interior of umpire satchel.

DESCRIPTION OF THE PREFERRED EMBODIMENT

For consistent usage in this disclosure, the nomenclature "compartment depth" is used to mean the vertical extent or vertical height dimension of the specific compartment with the satchel worn about the waist. Table 1 contains a tabulation of definitions of all special terminology employed in this disclosure.

Figure 1:
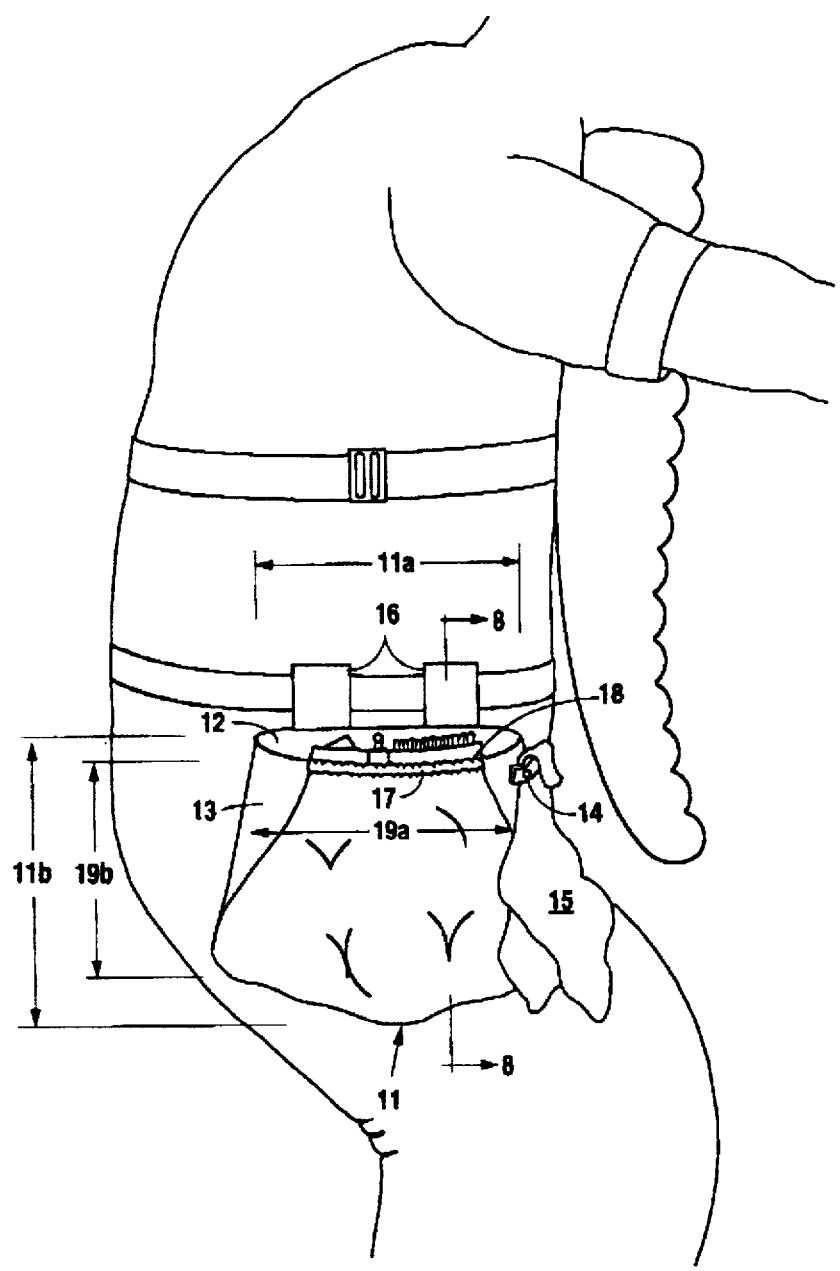
FIG. 1 discloses the general features of the umpire satchel of the present invention as being worn on a waistband by a right-handed person. A mirror-image configuration would be optimal for a left-handed person. As can be seen, the front-facing aspect of the satchel also carries a retainer loop for an absorbent wiper which is easily accessed by the wearer. The vertical section plane for FIG. 8 is indicated by arrows.
Figure 7:
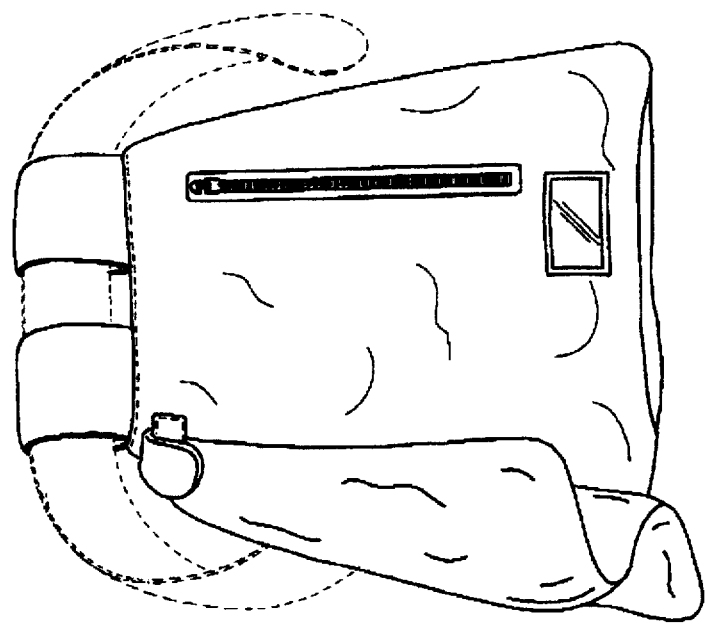
FIG. 7 shows the reverse side of the embodiment shown in FIG. 6. The vertical slide fastener and transparent window compartment are indicated.
Figure 8:
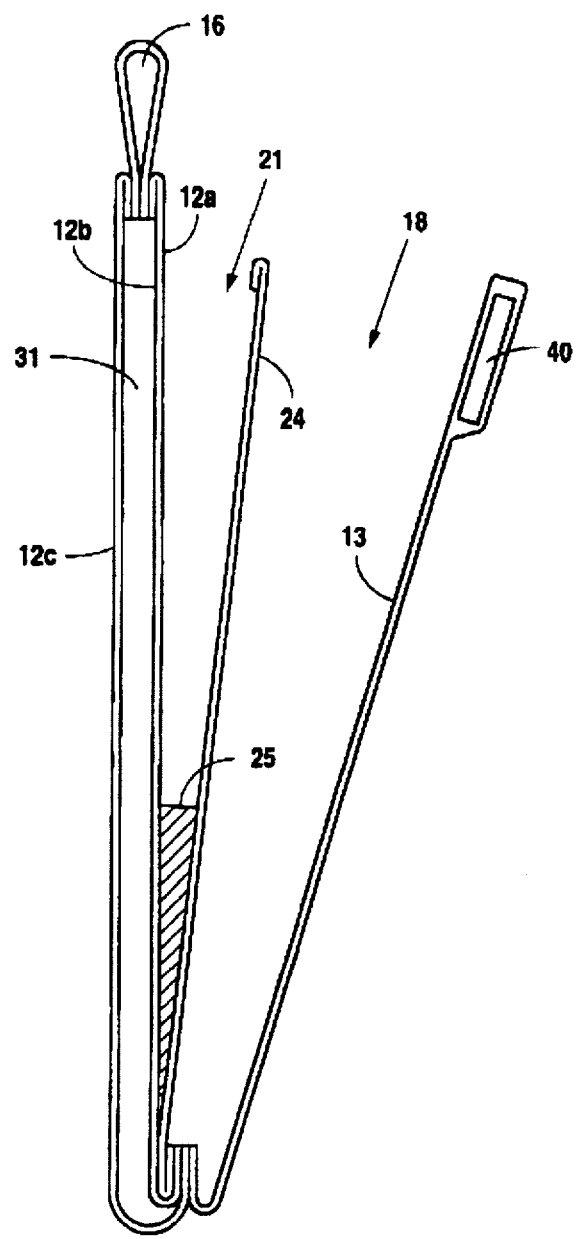
FIG. 8 shows a vertical section taken through the major rectangular compartment of the embodiment of FIG. 6; the location of the vertical cutting plane used is shown in FIG. 1. In this embodiment, the frontwall is double thickness and the depth of the major rectangular compartment extends to the lower edge of the satchel.

FIG. 1 shows an in-use view of the umpire satchel (11) of this invention being worn on the right hip as would be convenient for a right-handed person. The satchel is formed by cutting and lockstitching flat fabric pieces into the embodiments shown in FIGS. 1–8. Various knit, woven or non-woven fabrics with natural, synthetic and blended fibers such as broadcloth, duck, spunbonded olefin, ballistic nylon, etc., can be used for any of the panels or patch compartments. Decorative and reinforcing tapes/welts, etc., of a contrasting color or texture may be used on the principal panels and for binding major-edge seams. Laminated or coated fabrics may be used for additional water repellency and abrasion resistance of major panels. The backwall includes patch-type compartments on its interior (12a) and exterior (12b) surfaces; a full-size patch is shown in FIG. 8. The exterior fabric-patch layer also forms the back enclosure panel of the gameball compartment. The gameball compartment is indicated schematically as (18). The top zone of backwall interior panel (12a), which faces outward from the wearer's body and extends somewhat above the frontwall panel (13), is fitted with patch-type compartments sized for the specific items of equipment shown, e.g., plate brush, writing instrument (pen/pencil/input recording stylus) and ball/strike counter which can be accessed quickly with the right hand. These compartments are formed of fabric as surface-patch compartments attached to the outward-facing surface of the backwall interior panel (12a).

As shown, the vertical depth aspect of each of these compartments is adapted for secure enclosure of a major portion of the specific equipment item, and to leave an easily-grasped portion exposed for quick grasping. If, due to different physical sizes of different brands of equipment, the compartment is too large, a removable plastic insert, (25), as shown in FIG. 8, can be cut to fill the lower portion and give optimal exposure of the device from the top edge of the compartment. The gameball compartment, GBC, is formed between the backwall panel and the frontwall panel (13).

Three major edge-closure seams, i.e., side and bottom seams define the length and depth dimensions of the gameball compartment. The top aspect of the gameball compartment is an opening with a stretchable, elastic element attached to the frontwall. When the gameball compartment is empty, the elastic element, which is stitched in place under tension, causes the formation of gathers in the top edge of the frontwall. The gathered zone between the lateral ends of the elastic element is identified as the stretch zone of the frontwall (17). The opening and its degree of stretch is appropriate to accommodate even a large man's hand holding a gameball, as would be needed for inserting a ball into the compartment. Similarly, the elastic compliance must be appropriate to encompass at least three balls securely under anticipated body movements and postures of the wearer. The gameball compartment is sized to contain at least three balls. The absorbent wiper, (15), is of appropriate size for use in cleaning game equipment and

TABLE 1

Feature Nomenclature and Indicia

| INDICIA | DEFINITION OF NOMENCLATURE | FIG. | Dimension Range min, mm | max, mm |
|---|---|---|---|---|
| 11 | umpire satchel, shown on right hip of wea | 1 | na | na |
| 11a | satchel width, horizontal | 1 | 150 | 350 |
| 11b | satchel depth, vertical | 1 | 200 | 320 |
| 13 | frontwall panel | 1 | na | na |
| 14 | fixed anchor loop for engagement with wi | 1 | na | na |
| 15 | wiper with engagement fastener for ancho | 1 | na | na |
| 16 | satchel suspension loops, length × width | 1 | 50 × 20 | 100 × 90 |
| 17 | frontwall stretch zone, width | 1 | 160 | 300 |
| 18 | gameball compartment, GBC | 1 | na | na |
| 19a | width dimension of GBC | 1 | 160 | 290 |
| 19b | depth dimension of GBC | 1 | 180 | 300 |
| 21 | major rectangular compartment, MRC | 2 | na | na |
| 21a | width dimension of MRC | 2 | 60 | 150 |
| 21b | depth dimension of MRC | 2 | 100 | 200 |
| 22 | stylus compartment, MC | 2 | na | na |
| 22a | width dimension of MC | 2 | 20 | 50 |
| 22b | depth dimension of MC | 2 | 110 | 190 |
| 23 | counter compartment, CC | 2 | na | na |
| 23a | width dimension of CC | 2 | 70 | 150 |
| 23b | depth dimension of CC | 2 | 80 | 150 |
| 24 | patch panel, fitted compartments | 8 | | |
| 25 | removable insert | 8 | na | na |
| 31 | envelope compartment, EC | 3 | na | na |
| 31a | width of envelope compartment | 3 | 80 | 180 |
| 31b | depth of envelope compartment | 3 | 100 | 300 |
| 32 | vertical opening for hand access | 3 | 120 | 180 |
| 32a | length of slide fastener for hand access | 3 | 130 | 190 |
| 33 | transparent window compartment, length | 3 | 30 × 60 | 100 × 150 |
| 40 | elastic element, EE | 4 | na | na |
| 41 | contracted length dimension of elastic ele | 4 | 110 | 300 |
| 42 | maximum extended length of EE | 4 | 120 | 400 |
| 51 | central expansion pleat, EP | 5 | na | na |
| 52 | maximum depth of EP | 5 | 100 | 300 |
| 53 | max extension provided by EP | 5 | 50 | 150 |
| 64 | shaped, absorbent wiper, area, approx. 0. | 5 | 150 × 15 | 400 × 400 |
| 65 | engageable fastener integral | 5 | na | na |

TABLE 1-continued

Feature Nomenclature and Indicia

| INDICIA | DEFINITION OF NOMENCLATURE | FIG. | Dimension Range min, mm | max, mm |
|---|---|---|---|---|
| | w. wiper | | | |
| 12a | backwall interior surface | 8 | na | na |
| 12b | backwall exterior surface | 8 | na | na |
| 12c | fabric overlay panel, backwall | 8 | | | for personal use of the umpire; one edge or corner is releasably attached to the satchel by means of an anchor loop, (14). The belt suspension loops, (16), are of appropriate size and strength to men's or women's apparel belts and the weight of the fully-loaded satchel.

Figure 2:
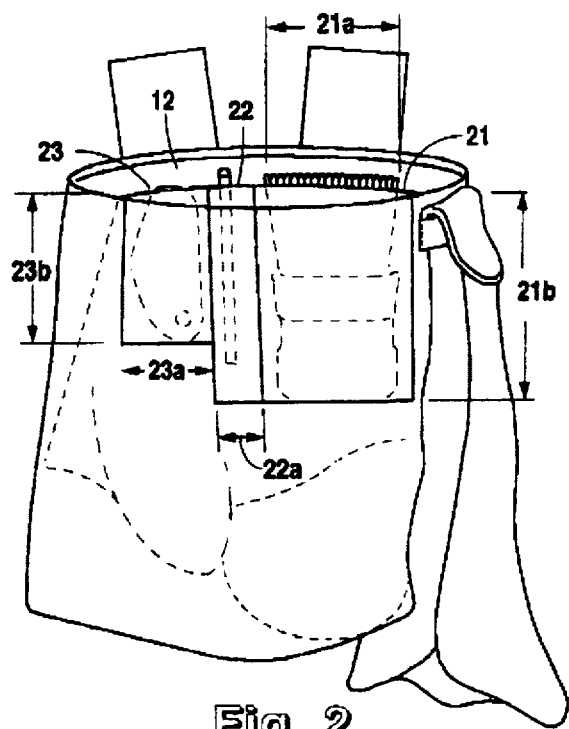
FIG. 2 discloses an interior view, with the frontwall panel cutaway, of the backwall panel and its three fitted interior compartments for equipment.

FIG. 2 is a cut-away view of the umpire satchel laid flat on its exterior backwall surface (12b) with the frontwall panel (13) removed, as indicated by dashed lines, and the backwall interior surface (12a) is facing outward. This view shows additional size and positioning detail for the three fitted equipment compartments. The major rectangular compartment, MRC, is designated generally as (21). The width dimension of the MRC is designated as (21a); the MRC depth dimension is shown as (21b). The MRC compartment is sized to accommodate a brush which is indicated by an outline showing the bristles pointed upward. The stylus compartment, SC, is designated generally as (22); its width dimension is indicated as (22a). The depth dimension of SC can range from 80–150 percent of the MRC depth, i.e., 0.8 (21b) to 1.5 (21b). The SC compartment is sized to accommodate 1–3 writing implements such as markers, pens or pencils; a single pencil-type implement is shown in outline with the eraser-end upward. The nomenclature stylus has been deliberately chosen to include stylus-like electronic, optical, and magnetic implements or scanners used by the umpire in data acquisition/recording. The counter compartment, CC, is designated generally as (23); its width and depth dimensions are (23a) and (23b) respectively. The CC compartment is sized to accommodate a counter which is shown by an outline. As can be seen, the usable depth of the gameball compartment is approximately the depth dimension (21b) plus 1 to 1.5 gameball diameters.

Figure 3:
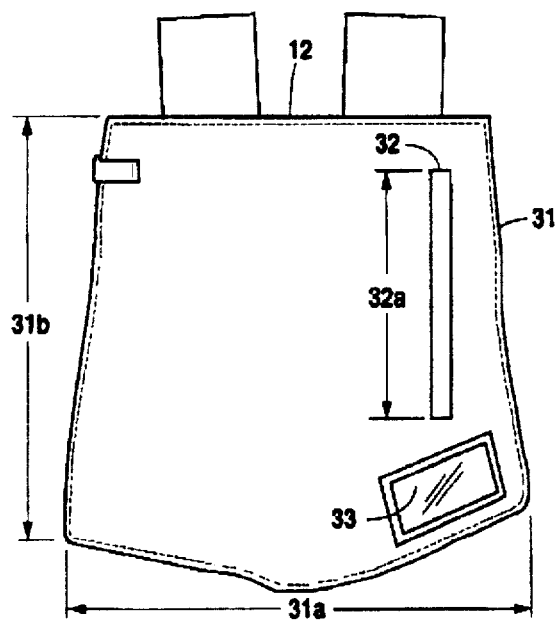
FIG. 3 discloses an exterior view of the backwall of the satchel showing the envelope compartment and the placement of the vertical opening and slide closure device. Also shown is an optional transparent window compartment for an auxiliary ID card for personal/emergency medical data.

FIG. 3 is a view with the umpire satchel laid flat on its frontwall (13) with the exterior surface of the panel (12c) facing outward. This view shows additional size and positioning detail for the envelope compartment, EC, which is generally designated as (31). The total width and depth dimensions of the EC are indicated as (31a) and (31b) respectively. This compartment is designed to hold various small personal accessories and can be accessed by the vertical opening (32) sized and positioned close to the vertical edge to permit convenient hand access without the risk of accidental loss of loose, small items also in this compartment as the hand is withdrawn. This opening is closed by a slide fastener of length just sufficient to allow easy passage of even a large man's hand; this length is designated (32a). For maximum security, the closed position of the slider is at the uppermost or top end of the fastener. The lateral spacing of the opening from the adjacent satchel edge is preferably in the range 20–50 mm for easy right-hand access. FIG. 3 also shows one alternative placement of the transparent-window compartment (33) on the lower exterior zone of panel (12c). This transparent-window is shown with a double-line picture-frame rim around its periphery.

Figure 4:
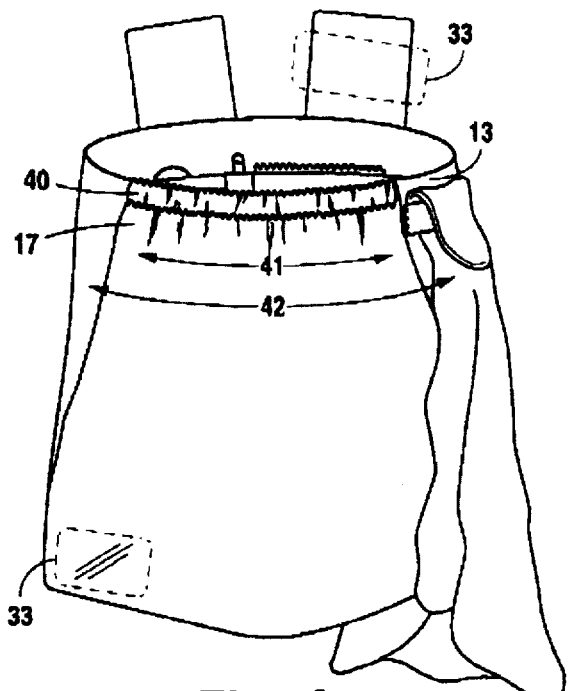
FIG. 4 discloses general features, construction and size proportions of the elastic element in the frontwall panel.

FIG. 4 is a view of the upper access opening of the frontwall panel (13) showing additional detail for the sizing and positioning of a single elastic element, EE. FIG. 4 also shows two alternative placement options for a transparent window compartment (33) to hold ID items which must be displayed for security. In other embodiments, a transparent badge window can be attached by a cord or strap to the wiper anchor. The contracted and extended lengths of EE are shown as (41) and (42) respectively. The elastic element is centered along the top edge of the frontwall panel. If needed, multiple or longer elastic elements might be used to accommodate larger hands or bagged/enclosed gameballs.

Figure 5:
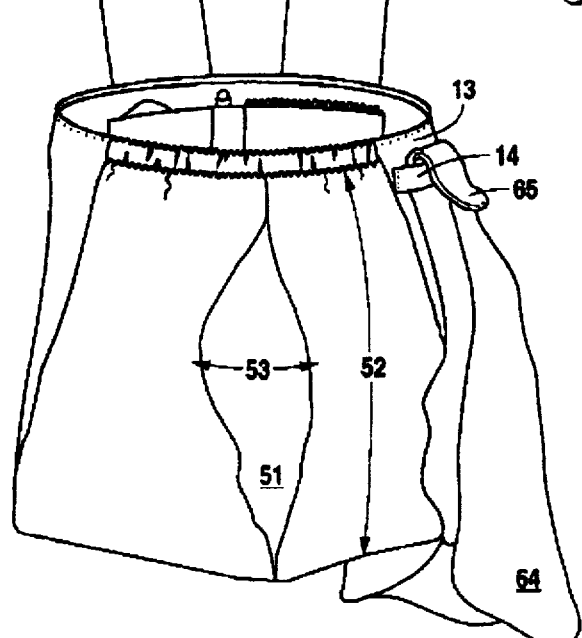
FIG. 5 discloses general features, construction and size proportions of the expansion pleat in the frontwall panel, including the central expansion pleat.

FIG. 5 shows an alternative embodiment with a single expansion pleat in the frontwall below the elastic element. This pleat structure allows an expansion of at least 50 mm. The approximate vertical extent of this pleat is 150–200 mm. This optional feature allows the gameball compartment to hold 4 softballs or 8 baseballs. Multiple or larger expansion pleats may be used for increased volume and form shaping. An absorbent, rectangular fabric wiper (64) of adequate area in the range 0.05 to 0.3 sq. meters and required color may be releasably attached to the anchor loop (15) on the satchel. The wiper can be secured to the anchor loop by threading a shaped edge zone or one corner through the anchor loop and fastening the free end of the tip back to the wiper by means of an integral fastener (65). Washable alternative integral fasteners (65) for the wiper include snaps, buttons or hook-and-loop types.

Figure 6:
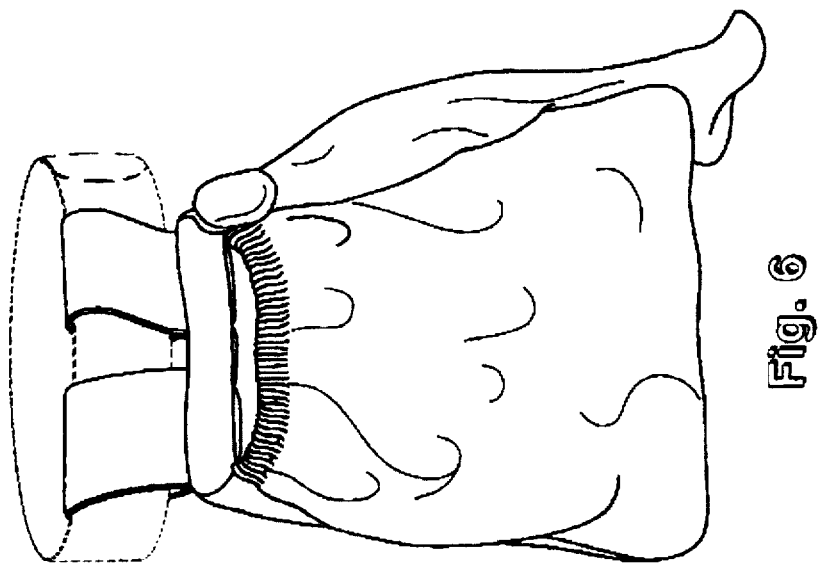
FIG. 6 shows the exterior view of an embodiment of the present satchel for a specific league as shown in Table 3; this embodiment does not have a central expansion pleat for the gameball compartment.

FIG. 6 is an external view of right-hip embodiment adapted to preferences of a selected league and shows the positioning of the upper edges of the fitted compartments with respect to the frontwall upper edge. FIG. 7 shows the reverse side of the embodiment in FIG. 6 and the transparent and envelope compartments.

FIG. 8 shows a cross-section view of the satchel and the relationship of the frontwall and overlay fabric layers of an embodiment for a selected league.

Table 1 shows a summary of the special nomenclature used to describe the features of the umpire satchel of this invention. The third column of this table provides a handy reference link between the feature name and its numeric indicia used in the figures. Because of the predominance of right-handedness, all the figures show a right-hand version. To accommodate for left-handed users, a mirror-image version is more appropriate. In the case of ambidextrous individuals, it is possible that some features such as the wiper anchor (14) and envelope compartment hand access (32) can be placed according to personal preference. It is anticipated that at least 4 basic embodiments will be offered in addition to customized versions i.e., every feature, material, component and dimension adapted for a handicapped person or anatomic anomaly.

EXAMPLES

The examples A–D presented below, along with Tables 1–3 indicate some alternative embodiments of the present invention.

Example A

Alternative Fabrics

Satchels according to this invention can be made from a wide variety of woven, knit and nonwoven fabric materials with diverse textures and physical properties. The various fabrics can be made with continuous-filament or staple yarns using either natural or synthetic fibers. Some alternative woven fabrics are:

A1. polyamide (nylon) plain weave—5.1 oz/yd$^2$; 23 warp× 21 fill, threads per inch; 840 warp×840 fill yarn denier, single ply; producer twist.

A2. polyamide (nylon) basket weave—13 oz/yd$^2$, 45 warp× 41 fill threads per inch; 1050 warp×1050 fill yarn denier, single ply; 2.75 Z warp×2.75 Z fill twist.

A3. polyester (Dacron) plain weave—5.4 oz/yd$^2$; 23 warp× 21 fill threads per inch; 220 warp×220 fill yarn denier, both 4-ply; producer twist.

A4. polyester (Dacron) 2/2 chain twill—10.4 oz/yd$^2$; 66 warp×42 fill, threads per inch; 220 warp×220 fill yarn denier, both 3-ply; producer twist in singles; 4S warp×4S fill twist in plies.

A5. polypropylene 5-harness sateen—5.75 oz/yd; 52 warp× 44 fill threads per inch; 210 warp×210 fill yarn denier, both 2 ply; producer twist in singles; 5.5S warp×5.5S fill twist in plies.

A6. urethane-coated polyester-cotton fabric—water-repellent panels, compartments A7. siloxane surface-treated fabric, like Scotchguard™ sprayed on polyester-cotton fabric—water-repellent panels, compartments A8. knit fabric—esp. cotton-terry toweling—absorbent wiper A9. non-woven fabric like Tyvek™ or Remay™ spun-bonded polyolefins—compartments, panels Table 2. shows a summary of preferred colors and materials of construction used for preparation of official umpire satchels as selected by one league. The combination presented reflects the tradition of the sport and the standards of the particular league for appearance and function. Within the scope of this invention, other fabric materials, layouts and manufacturing methods can be used within the parameters of woven, nonwoven, knit, laminated/coated fabrics as might be desirable for special characteristics.

Example B

Alternative Seams, Trim, Fasteners, Etc.
B1. Panel-Edge Seams
B1.1 Single-row lockstitch, plain with overcasting, everted
B1.2 Single-row stretch zigzag, plain with overcasting, everted
B1.3 Single-row lockstitch, flat-felled
B1.4 Single-row stretch zigzag, flat-felled
B1.5 Ultrasonic bonded seam, plain, 1–5 mm width
B1.6 Adhesive-bonded seam, plain, turned 1–5 mm width
B1.7 Binding-taped panel-edge seams
B2. Compartment-Edge Seams or Fasteners
B2.1 Single-row lockstitch, turned cut edge
B2.2 Single-row stretch zigzag, turned cut edge
B2.3 Ultrasonic bonded seam, 1–5 mm width
B2.4 Adhesive-bonded seam, 1–5 mm width
B2.5 Bar-tacked compartment, edges, seams
B2.6 Mating hook-and-loop strips for adjustment of width, depth
B2.7 Mating snaps for adjustment of width, depth
B3. External Trim/Decoration
B3.1 Tape binding, major panel edges, spec. color/texture/stitching
B3.2 Adhesive or ultrasonic-bonded patch w. embroidered designs
B3.3 Embroidered design on panel external surface
B3.4 lifting ribbon or pull-tab for elevating contents of fitted compartments
B4. Fasteners
B4.1 Slide zipper, metal or plastic, panel-matching color, 250 mm length
B4.2 Snaps to close compartments, 7–12 mm diam., bright plating or black anodized
B4.3 Snaps or buttonholes for external straps, panel-matching color, 7–15 mm diam.
B4.5 Buttons for external straps
B4.6 Clips w. safety latch for attaching external items, bright plating or black anodized
B4.7 D-rings for attaching external items, bright plating or black anodized
B4.8 Flaps, tie-loops or other fasteners/closures to close compartments, panel-matching color.
B5. Other Construction Features
B5.1 Special security closures for compartments including magnetic clips, hook-and-loop tabs
B5.2 Integrated belt with length-adjustment devices made of metal or polymer, 25–75 mm width, 0.5–1.5 meter girth
B5.3 Removable internal panel containing multiple fitted compartments with snaps or hook-and-loop fasteners for easy, secure attachment to satchel backwall interior surface
B5.4 Removable, closeable biohazard bag for releasable insertion into gameball compartment and fitted with mating external snap or hook-and-loop fasteners to engage with elements fixed on GBC interior Example C Alternative Configurations C1. Right/Left Hand placement, ordering and total number of fitted compartments.

Depending upon handedness of wearer, league rules and personal preferences, 1–5 fitted compartments can be arranged in several different left-to-right orders across the interior backwall panel.

C2. Right/Left Hand placement of vertical slide fastener and wiper anchor loop.

Depending upon handedness of the wearer and league preferences, either the vertical slide fastener or the anchor loop may be positioned for maximum wearer convenience. Another alternative embodiment would be the use of dual slide fasteners and anchor loops.

Example D

Alternative Satchel and Compartment Dimensions

Basic dimensions of the satchel are dictated by the diameter of the game ball and league regulations. Relative to ball size, the diameter of a regulation-size baseball is approx. 73 mm, while the std. diameters of softballs are approx. 89 mm and 97 mm for women's-league or men's-league, respectively. Each league has specific rules for the number of game balls which must be held in reserve in the satchel.

The form of the present satchel can be scaled for different-sized balls by linear scaling on the basis of ball diameter. Thus, satchel dimensions as defined in Table 1 are scaleable over a range of at least plus or minus 35% for different leagues.

The specific width and depth dimensions of each fitted compartment is dictated by the specific types/brands/models of equipment approved or required by the league. For example, a simple mechanical counter may be much smaller and thinner than a battery-powered electronic counter with input keys and a display. The dimensions of rectangular fitted compartments are scaleable over a range of 50–300% according to the size and shape of specific items to be contained. Alternative embodiments of this satchel may include special curvilinear-shaped, expansible/elastic/pleated, non-rectangular compartments or special external hangers for hand-held telemetry signaling devices which relay umpire inputs to the scoreboard or store data directly into league computerized records.

For the situation of an official who may need a customized set of fitted compartments, it is anticipated that a removable panel containing multiple fitted compartments could be attached as a single unit to the present satchel. For this case, snaps, buttons and hook-and-loop fasteners would be useful.

Table 3. shows a summary of the preferred physical dimensions of the umpire satchel for use in one league. The specific size and placement combination presented reflects the tradition of the sport and the standards of the particular league for appearance and function. FIGS. 6, 7 and 8 show appearance and construction of one embodiment.

Within the scope of this invention, many other combinations of length, width, size, texture, fasteners, flaps, etc., are possible without departing from the spirit and scope of this disclosure.

TABLE 2

Construction Guidelines for League A Regulations

| Feature(s) name | Material (black color) | Example/data |
|---|---|---|
| frontwall, backwall | polyester, plain weave, 60 × 60, 300–600 g/m2 | duck, cotton-polyester |
| wiper | absorbent toweling | cotton or blends |
| seam stitching | polyester, lockstitch | matching color |
| slide fastener | metal or polymer | matching color |
| suspension loops | woven, non-woven, knit | matching color |
| elastic | rubber core, polyester | 6 mm width |

TABLE 3

Size Preferences for League A

| Feature(s) ID | Dimension | Min, mm | Max, mm |
|---|---|---|---|
| 11a | satchel width | 200 | 400 |
| 11b | satchel depth | 200 | 400 |
| 16 | loop length | 120 | 300 |
| 16 | loop width | 40 | 80 |
| 41 | elastic, contracted | 150 | 300 |
| 42 | elastic, stretched | 200 | 400 |

I claim:

1. A wearable device for carrying a plurality of game balls and for carrying umpire equipment, said device comprising:

a satchel having first, second, and third fabric panels, each of said panels having a pair of opposed generally parallel side edges, a bottom edge generally perpendicular to said side edges, and a top edge generally parallel to said bottom edge, each of said panels having similar width and height dimensions, said bottom and side edges of said first and second panels being respectively sewn together to form an open-topped game ball compartment defined by said top edges and interior sides of said first and second panels, said game ball compartment being sized for enclosing at least three game balls and adapted for entry of a human hand therein for transferring said game balls to or from said game ball compartment, said top edge of said first panel including an attached elastic shortening element extending substantially parallel thereto, said element being attached in an extended state drawing said side edges of said front panel together for reducing the perimeter of said open-topped compartment to provide a means to retain the game balls in said game ball compartment, said bottom, top, and side edges of said second and third panels being respectively sewn together to form a fully-enclosed envelope compartment between said second and third panels, and means provided on said third panel for providing access to said envelope compartment;

a side-by-side, group of three open-topped interior compartments consisting of a main rectangular compartment, a stylus compartment, and a counter compartment, each of said interior compartments being sized for securely holding and presenting a selected item of umpire equipment therein with at least an end portion thereof exposed above an open top of said interior compartment to allow easy grasping of the equipment, each said interior compartments being formed by an overlay panel connected to said second panel and located within said game ball compartment wherein each of said interior compartments being defined by a pair of side seams, a bottom seam generally perpendicular to at least one of said side seams, an open top edge defining said open top generally perpendicular to at least one of said side seams, each said open top edge of said interior compartments being positioned adjacent to and substantially parallel with said top edge of said second panel;

an exterior attachment means for releasable engagement with an absorbent wiper being provided on an exterior side of said third panel adjacent said top edge thereof, and at least one suspension loop in connection with said satchel, said at least one loop adapted to removably receive a support band encircling a wearer's body.

2. The device of claim 1 wherein said access means for entry into said envelope compartment comprises:

(a) a vertical slit aperture length sized to admit a large adult hand, located approximately parallel to one of said edges of said third panel and positioned so that the lower end of said aperture lies somewhat above said bottom edge of said third panel, and (b) a known, full-length slide fastener for closing said slit aperture oriented such that the slider is at said lower end of said slit when said slide fastener is in its full-open state; and wherein said satchel is fitted with two said suspension loops extending upward from said top edge of said second and third panels.

3. The device of claim 2 wherein said stylus compartment is positioned between said main rectangular and counter compartments.

4. The device of claim 3 wherein, (a) said slide fastener is one of: metal zipper and plastic zipper, and (b) said color of said thread, fabric panels and fasteners is uniform.

5. The device of claim 4 prepared as a version to be worn on the right hip of the wearer wherein, (a) said panel fabric construction is one of: woven, knit and non-woven, (b) said panel fabric weight is in the range 5.1 ounces/(yard)2 to 600 grams/(meter)2, (c) said main rectangular compartment lies adjacent a ventral surface of the wearer's body, and (d) said envelope compartment hand access means lies adjacent a dorsal surface of the wearer's body.

6. The device of claim 5 wherein:
(a) the width of the top opening of the main rectangular compartment is in the range 60–150 mm,
(b) the width of said stylus compartment is in the range 20–50 mm,
(c) the width of said counter compartment is in the range 70–150 mm, and
(d) the depth of each said interior compartment is individually adjusted by fixing the distance from its top edge to its bottom seam to provide an optimal vertical exposure of selected said equipment therein.

7. The device of claim 6 wherein a known, enclosed, transparent-plastic document compartment is attached to the exterior surface of said third panel, said document compartment being sized to securely encompass a typical photo-ID card.

8. The device of claim 5 prepared as a version to be worn on one of the hips on the wearer's body.

9. The device of claim 3 wherein at least one of said first, second, third and overlay panels is prepared of known water repellent fabric.

10. The device of claim 5 wherein at least one of: said first, second, third and overlay panels is prepared of known water repellent fabric.

* * * * *